United States Patent
Ornstein

(10) Patent No.: US 7,247,644 B2
(45) Date of Patent: Jul. 24, 2007

(54) ESTER DERIVATIVES OF A DECAHYDROISOQUINOLINE-3-CARBOXYLIC ACID AS ANALGESTICS

(75) Inventor: Paul Leslie Ornstein, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 22 days.

(21) Appl. No.: 10/511,452

(22) PCT Filed: Apr. 14, 2003

(86) PCT No.: PCT/US03/10466

§ 371 (c)(1),
(2), (4) Date: Oct. 14, 2004

(87) PCT Pub. No.: WO03/091243

PCT Pub. Date: Nov. 6, 2003

(65) Prior Publication Data

US 2005/0256155 A1 Nov. 17, 2005

(51) Int. Cl.
A61K 31/47 (2006.01)
C07D 217/18 (2006.01)
(52) U.S. Cl. .................. 514/307; 546/147
(58) Field of Classification Search .......... 546/147; 514/307
See application file for complete search history.

(56) References Cited

U.S. PATENT DOCUMENTS

| 4,902,695 A | 2/1990 | Ornstein |
| 5,356,902 A | 10/1994 | Ornstein |
| 5,446,051 A | 8/1995 | Ornstein |
| 5,670,516 A | 9/1997 | Arnold et al. |
| 5,675,008 A | 10/1997 | Bertsch et al. |
| 5,767,117 A | 6/1998 | Moskovitz |

FOREIGN PATENT DOCUMENTS

| EP | 0 590 789 | | 4/1994 |
| WO | WO 8801615 | * | 3/1988 |
| WO | WO 98/45270 | | 10/1998 |
| WO | WO 01/01972 | | 1/2001 |
| WO | WO 01/02367 | | 1/2001 |
| WO | WO 01/46173 | | 6/2001 |
| WO | WO 02/053555 | | 7/2002 |
| WO | WO 02/053556 | | 7/2002 |
| WO | WO 03/024453 | | 3/2003 |
| WO | WO 03/024934 | | 3/2003 |
| WO | WO 03/082856 | | 10/2003 |

OTHER PUBLICATIONS

Schoepp, Meurophamacology, vol. 34(9), 1159-1168, 1995.*
Bundgaard, J of Med Chem, vol. 28 (8), 979-981, 1985.*
Wang, Current Medicinal Chemistry, vol. 7, pp. 437-453, 2000.*
Wang Current Medicinal Chemistry, vol. 7, pp. 437-453, 2000.*
Stinchcomb, Pharmaceutical Research, vol. 13, No. 10, pp. 1519-1523, 1996.*
Stinchcomb, J of Pharmaceutical Sciences, vol. 91, No. 12, pp. 2571-2578, 2002.□□.*
Doh, J of PHarmaceutical Scences, vol. 92, No. 5, pp. 1008-1017, 2003.*
Kao, Pharmaceutical Research, vol. 17, No. 8, pp. 978-984, 2000.*
Bibby, International Journal of Pharmaceutics, vol. 144, pp. 61-70, 1996.*
Bleakman, et al., "Pharmacological Discrimination of GLUR5 and GLUR6 Kainate Receptor Subtypes by (3S,4AR,6R,8AR)-6-2-(1(2)H-Tetrazole-5-yl)Ethyl Decahydroisoquinoline-3 Carboxylic Acid," Molecular Pharmacology, Baltimore, MD, vol. 49, No. 4, pp. 581-585; XP000942899 (1996).
Buchwald, P. and Bodor, N., Quantitative Structure-Metabolism Relationships: Steric and Nonsteric Effects in the Enzymatic Hydrolysis of noncongener Carboxylic Esters, J. Med. Chem. 42, 5160-5168, 1999.
Tanino, T., Ogiso, t., Iwaki, M., Tanabe, G. and Muraoka, O., Enhancement of Oral Bioavailability of Phenytoin by Esterification, and in vitro Hydrolytic Characteristics of Prodrugs, International Journal of Pharmaceutics 163, 91-102, 1998.
Shindo, H. Fukuda, K., Kawai, K. and Tanaka, K., Studies on Intestinal Absorption of Pivampicillin and Species Difference in the Intestinal Esterase Activity, J. Pharm. Dyn. 1, 310-323, 1978.
O'Neill, MJ, et al., "Decahydroisoquinolines: Novel competitive AMPA/kainite antagonists with neuroprotective effects in global cerebral ischaemia," *Neuropharmacology*, 37, pp. 1211-1222 (1998).
Sahara, Y, et al., "Glutamate receptor subunits GluR5 and KA-2 are coexpressed in rat trigeminal ganglion neurons," *The Journal of Neuroscience*, 17(17), pp. 6611-6620 (1997).
Alam, Z., et al., "Plasma levels of neuroexcitatory amino acids in patients with migraine or tension headache," *Journal of Neurological Sciences*, 156, pp. 102-106 (1998).

(Continued)

Primary Examiner—D. Margaret Seaman
(74) Attorney, Agent, or Firm—Alexander Wilson

(57) ABSTRACT

Thus, the present invention provides compounds of formula (I) The present invention further provides the use of a compound of formula (I) for the manufacture of a medicament for the treatment of a neurological disorder. The present invention further provides the use of a compound of formula (I) for the manufacture of a medicament for the treatment of pain or migraine

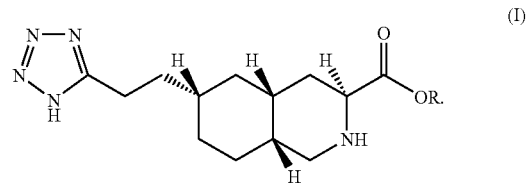

(I)

20 Claims, No Drawings

OTHER PUBLICATIONS

Ornstein, et al., Structure-Activity Studies of 6-Substituted Decahydroisoquinoline-3-carboxylic Acid AMPA Receptor Antagonists. 2. Effects of Distal Acid Bioisosteric Substitution, Absolute Stereochemical Preferences, and in Vivo Activity, J. Med. Chem., vol. 39, No. 11, pp. 2232-2244 (1996).

Procter, et al., "Possible role of GluR5 glutamate receptors in spinal nociceptive processing in the anaesthetized rat," Journal of Physiology, XX, XX, vol. 405P, pp. 101P-102P; XP002108296 (1997).

Nakam, et al., "The search for AMPA/Gly(N) receptor antagonists," Drugs Future, vol. 24, No. 10, pp. 1107-1124; XP000997758 (1999).

Procter, et al., "Actions of kainite and AMPA selective glutamate receptor ligands on nociceptive processing in the spinal cord," Neuropharmacology, Oct.-Nov. 1998, 37 (10-11), pp. 1287-1297; XP000997628 .

Bleakman, "Kainate receptor pharmacology and physiology," Cellular and Molecular Life Sciences, 56/7-8 (558-566); XP000990931.

Simmons, et al., "Kainate GluR5 receptor subtype mediates the nociceptive response to formalin in the rat," Neuropharmacology, 37(1), pp. 25-36; XP000997629 (1998).

Database Medline "Online", US National Library of Medicine (NLM), Bethesda, MD, US; Mitsikostas D.D., et al, "Non-NMDA glutamate receptors modulate capsaicin induced c-fos expression within trigeminal nucleus caudalis," retrieved from DIALOG, Database accession No. 10003939; XP002165715 abstracct & British Journal of Pharmacology, Jun. 1999 (127 (3); pp. 623-630.

Slides that accompanied an oral presentation of the named inventor, Paul Leslie Ornstein, at Medicinal Chemistry Gordon Research Conference, Aug. 9, 2001, Colby Sawyer College, New Hampshire.

James Eckstein, Poster presentation "Disposition of the Novel AMPA Antagonist, LY293558, in Rats and Dogs Following Intravenous Administration" given at the American Association of Pharmaceutical Sciences meeting, San Diego, California, Jun. 1994.

* cited by examiner

ESTER DERIVATIVES OF A DECAHYDROISOQUINOLINE-3-CARBOXYLIC ACID AS ANALGESTICS

FIELD OF THE INVENTION

The present invention relates to novel prodrug forms of (3S,4aR,6R,8aR)-6-[2-(1(2)H-tetrazole-5-yl)ethyl-1,2,3,4,4a,5,6,7,8,8a-decahydroisoquinoline-3-carboxylic acid, to pharmaceutical compositions containing the prodrug forms, and to methods of using the prodrug forms.

BACKGROUND OF THE INVENTION

U.S. Pat. No. 5,670,516 discloses that certain decahydroisoquinoline derivatives are AMPA receptor antagonists, and as such are useful in the treatment of many different conditions, including pain and migraine. In addition, WO 01/02367 A3, published Jan. 11, 2001, discloses diester prodrug forms of the selective $GluR_5$ antagonist 3S,4aR,6S,8aR-6-(((4-carboxy)phenyl)methyl)-1,2,3,4,4a,5,6,7,8,8a-decahydroisoquinoline-3-carboxylic acid.

It is an object of the present invention to provide monoesters of (3S,4aR,6R,8aR)-6-[2-(1(2)H-tetrazole-5-yl)ethyl-1,2,3,4,4a,5,6,7,8,8a-decahydroisoquinoline-3-carboxylic acid which provide improved bioavailability of the parent monoacid in a patient. In addition, it is an object of the present invention to provide monoesters of (3S,4aR,6R,8aR)-6-[2-(1(2)H-tetrazole-5-yl)ethyl-1,2,3,4,4a,5,6,7,8,8a-decahydroisoquinoline-3-carboxylic acid which are substantially converted to the parent monoacid in the patient.

SUMMARY OF THE INVENTION

It has now been discovered that the novel monoesters of the monoacid, (3S,4aR,6R,8aR)-6-[2-(1(2)H-tetrazole-5-yl)ethyl-1,2,3,4,4a,5,6,7,8,8a-decahydroisoquinoline-3-carboxylic acid provide significantly improved bioavailability of the monoacid as compared to that provided by administration of the monoacid itself. In addition, the monoesters are substantially converted to the monoacid in the patient. The monoacid is disclosed in U.S. Pat. No. 5,670,516, issued Sep. 23, 1997.

Thus, the present invention provides compounds of formula I:

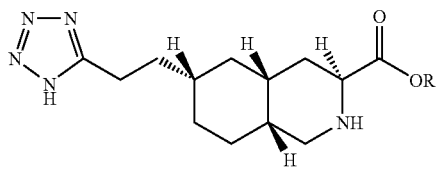

Formula I wherein R represents $C_1$-$C_{20}$ alkyl, $C_2$-$C_6$ alkenyl, $C_1$-$C_6$ alkyl-aryl, $C_1$-$C_6$ alkyl-($C_3$-$C_{10}$)cycloalkyl, $C_1$-$C_6$ alkyl-N,N—$C_1$-$C_6$ dialkylamine, $C_1$-$C_6$ alkyl-pyrrolidine, $C_1$-$C_6$ alkyl-piperidine, $C_1$-$C_6$ alkyl-morpholine or a pharmaceutically acceptable salt thereof.

The present invention further provides a method of antagonizing the AMPA or $GluR_5$ receptor, which comprises administering to a patient an effective amount of a compound of formula I.

In addition, the present invention provides a method for the treatment of a neurological disorder, which comprises administering to a patient in need thereof an effective amount of a compound of formula I.

The present invention further provides a method for the treatment of pain or migraine, which comprises administering to a patient in need thereof an effective amount of a compound of formula I.

The present invention further provides the use of a compound of formula I for the manufacture of a medicament for the treatment of a neurological disorder.

The present invention further provides the use of a compound of formula I for the manufacture of a medicament for the treatment of pain or migraine.

DETAILED DESCRIPTION OF THE INVENTION

As used herein, the term "prodrug" refers to a monoester derivative of a carboxylic acid functional drug, which derivative, when administered to a patient is converted into the monoacid (drug). The enzymatic and/or chemical hydrolytic cleavage of the compounds of the present invention occurs in such a manner that the parent monocarboxylic acid (drug) is released.

As used herein the term "Compound A" refers to (3S,4aR,6R,8aR)-6-[2-(1(2)H-tetrazole-5-yl)ethyl-1,2,3,4,4a,5,6,7,8,8a-decahydroisoquinoline-3-carboxylic acid.

As used herein the term "Compound B" refers to 6-[2-(2H-Tetrazol-5-yl)-ethyl]-decahydro-isoquinoline-3-carboxylic acid ethyl ester.

As used herein the term "Compound C" refers to 6-[2-(1H-Tetrazol-5-yl)-ethyl]-decahydro-isoquinoline-3-carboxylic acid 2-ethyl-butyl ester.

As used herein the term "Compound D" refers to 6-[2-(1H-Tetrazol-5-yl)-ethyl]-decahydro-isoquinoline-3-carboxylic acid isobutyl ester.

As used herein the term "Compound E" refers to 6-[2-(2H-Tetrazol-5-yl)-ethyl]-decahydro-isoquinoline-3-carboxylic acid 3-methyl-butyl ester.

As used herein the term "Compound F" refers to 6-[2-(1H-Tetrazol-5-yl)-ethyl]-decahydro-isoquinoline-3-carboxylic acid decyl ester.

As used herein the term "$C_1$-$C_4$ alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$C_1$-$C_6$ alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like. It will be understood that the term "$C_1$-$C_4$ alkyl" is included within the definition of "$C_1$-$C_6$ alkyl".

As used herein the term "$C_1$-$C_{10}$ alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like. It will be understood that the terms "$C_1$-$C_4$ alkyl" and "$C_1$-$C_6$ alkyl" are included within the definition of "$C_1$-$C_{10}$ alkyl".

As used herein the term "$C_1$-$C_{20}$ alkyl" refers to a straight or branched, monovalent, saturated aliphatic chain of 1 to 20 carbon atoms and includes, but is not limited to, methyl, ethyl, propyl, isopropyl, butyl, isobutyl, t-butyl, pentyl, isopentyl, hexyl, 3-methylpentyl, 2-ethylbutyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-nonadecyl, n-eicosyl and the like. It will be understood that the terms "$C_1$-$C_4$ alkyl", "$C_1$-$C_6$ alkyl", and "$C_1$-$C_{10}$ alkyl" are included within the definition of "$C_1$-$C_{20}$ alkyl".

As used herein, the terms "Me", "Et", "Pr", "iPr", "Bu" and "t-Bu" refer to methyl, ethyl, propyl, isopropyl, butyl and tert-butyl respectively.

As used herein the term "$C_2$-$C_6$ alkenyl" refers to a straight or branched, monovalent, unsaturated aliphatic chain having from two to six carbon atoms. Typical $C_2$-$C_6$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein, the term "aryl" refers to monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like.

As used herein, the term "$C_1$-$C_6$ alkyl-aryl" refers to a straight or branched, monovalent, saturated aliphatic chain of 1 to 6 carbon atoms which has an aryl group attached to the aliphatic chain. Included within the term "$C_1$-$C_6$ alkyl-aryl" are the following:

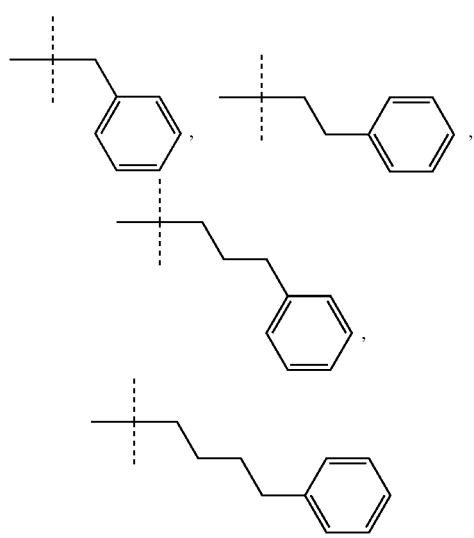

and the like.

As used herein the term "($C_3$-$C_{10}$)cycloalkyl" refers to a saturated hydrocarbon ring structure containing from three to ten carbon atoms. Typical $C_3$-$C_{10}$ cycloalkyl groups include cyclopropyl, cyclobutyl, cyclopentyl, cyclohexyl, cycloheptyl, cyclooctyl, and the like. It is understood that "($C_3$-$C_8$)cycloalkyl" and "($C_4$-$C_6$)cycloalkyl" is included within the term "($C_3$-$C_{10}$)cycloalkyl".

As used herein, the term "$C_1$-$C_6$ alkyl-($C_3$-$C_{10}$)cycloalkyl" refers to a straight or branched, monovalent, saturated aliphatic chain of 1 to 6 carbon atoms which has a ($C_3$-$C_{10}$)cycloalkyl attached to the aliphatic chain. Included within the term "$C_1$-$C_6$ alkyl-($C_3$-$C_{10}$)cycloalkyl" are the following:

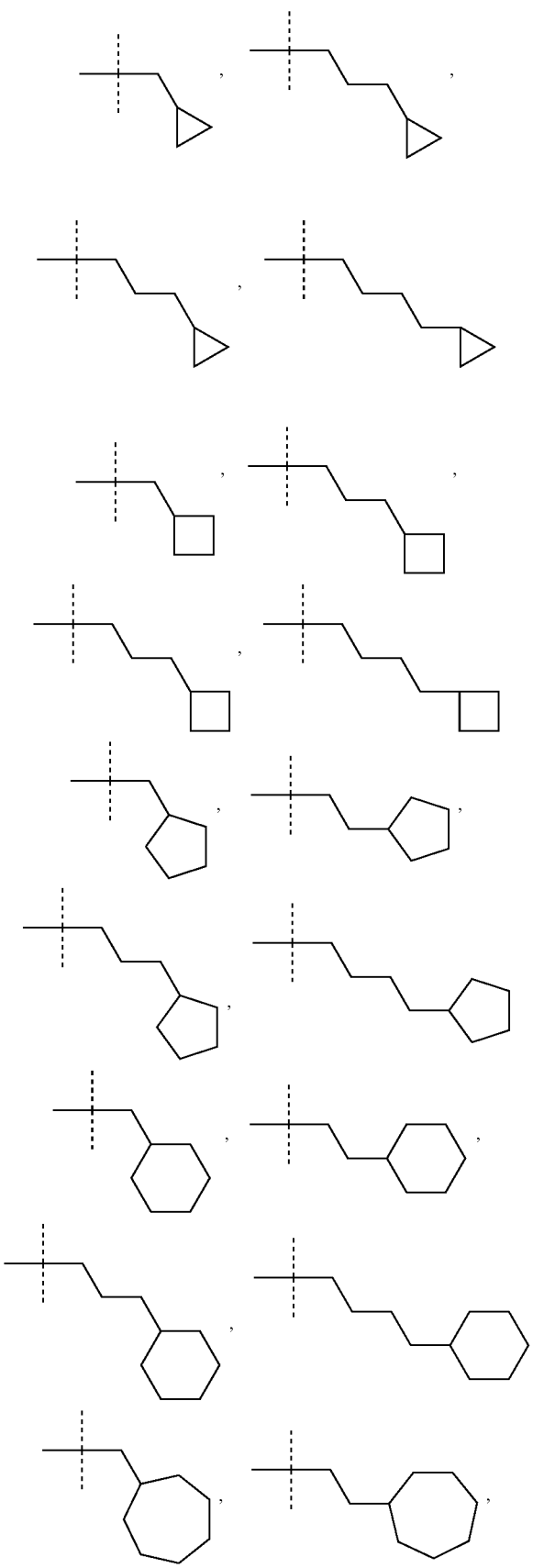

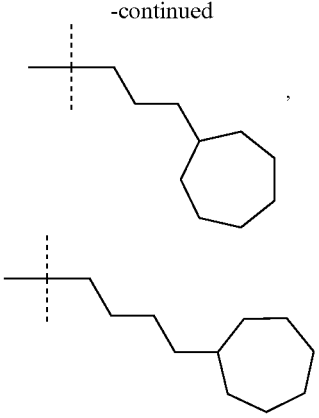

and the like.

As used herein the term "N,N—$C_1$-$C_6$ dialkylamine" refers to a nitrogen atom substituted with two straight or branched, monovalent, saturated aliphatic chains of 1 to 6 carbon atoms. Included within the term "N,N—$C_1$-$C_6$ dialkylamine" are —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$, and the like.

As used herein the term "$C_1$-$C_6$ alkyl-N,N—$C_1$-$C_6$ dialkylamine" refers to straight or branched, monovalent, saturated aliphatic chain of 1 to 6 carbon atoms which has an N,N—$C_1$-$C_6$ dialkylamine attached to the aliphatic chain. Included within the term "$C_1$-$C_6$ alkyl-N,N—$C_1$-$C_6$ dialkylamine" are the following:

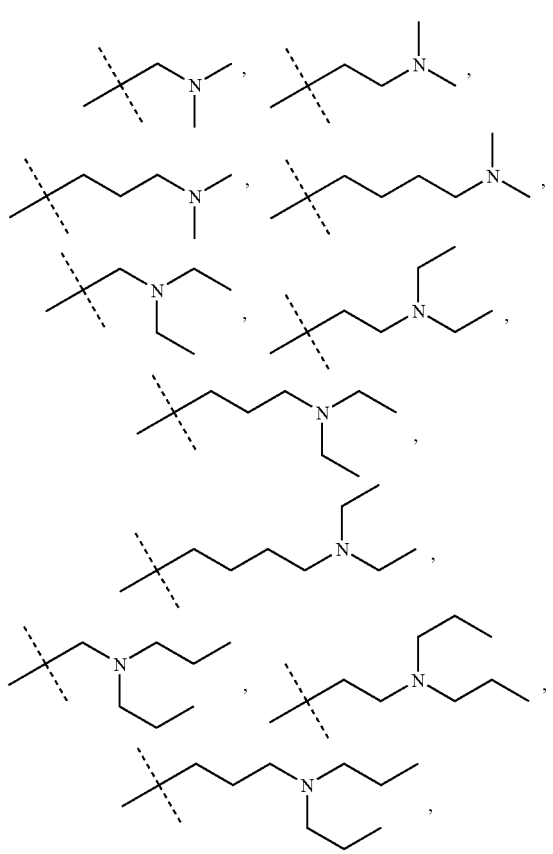

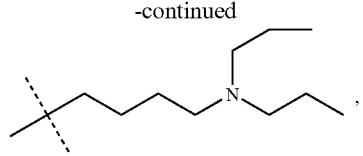

and the like.

As used herein the term "$C_1$-$C_6$ alkyl-pyrrolidine" refers to a straight or branched, monovalent, saturated aliphatic chain of 1 to 6 carbon atoms which has a pyrrolidine attached to the aliphatic chain. Included within the scope of the term "$C_1$-$C_6$ alkyl-pyrrolidine" are the following:

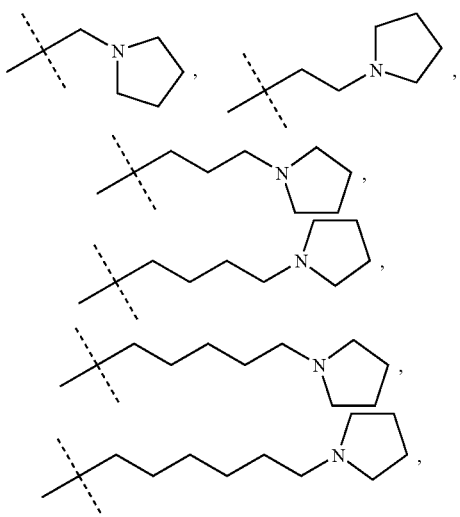

and the like.

As used herein the term "$C_1$-$C_6$ alkyl-piperidine" refers to a straight or branched, monovalent, saturated aliphatic chain of 1 to 6 carbon atoms which has a piperidine attached to the aliphatic chain. Included within the scope of the term "$C_1$-$C_6$ alkyl-piperidine" are the following:

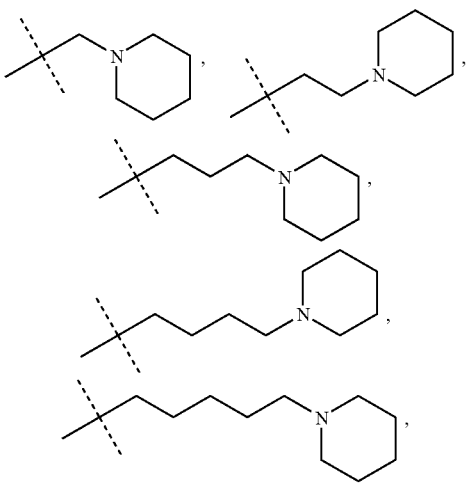

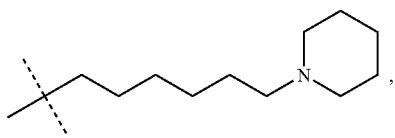

and the like.

As used herein the term "$C_1$-$C_6$ alkyl-morpholine" refers to a straight or branched, monovalent, saturated aliphatic chain of 1 to 6 carbon atoms which has a morpholine attached to the aliphatic chain. Included within the scope of the term "$C_1$-$C_6$ alkyl-morpholine" are the following:

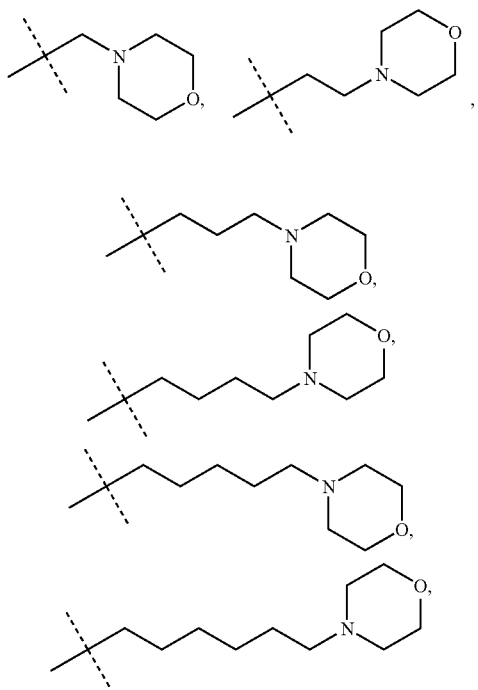

and the like.

The compounds of the present invention contain a tetrazole ring, which is known to exist as tautomeric structures. The tetrazole, having the double bond on the nitrogen atom at the 1-position and the hydrogen on the nitrogen atom at the 2-position is named as a 2H tetrazole and is represented by the following structure.

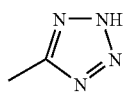

The corresponding tautomeric form wherein the hydrogen is at the nitrogen atom at the 1-position and the double bond on the nitrogen atom at the 4-position is named as a 1H-tetrazole. The 1H-tetrazole is represented by the following formula.

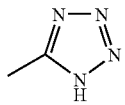

Mixtures of the two tautomers are referred to herein as 1(2)H-tetrazoles. The present invention contemplates both tautomeric forms as well as the combination of the two tautomers.

The designation "◀▬" refers to a bond that protrudes forward out of the plane of the page.

The designation "⦀⦀⦀" refers to a bond that protrudes backward out of the plane of the page.

This invention includes the hydrates and the pharmaceutically acceptable salts of the compounds of formula I. A compound of this invention can possess a sufficiently basic functional group which can react with any of a number of inorganic and organic acids, to form a pharmaceutically acceptable salt.

The term "pharmaceutically acceptable salt" as used herein, refers to salts of the compounds of formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, trifluoroacetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, trifluoroacetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid, oxalic acid, triofluoroacetic acid, and methanesulfonic acid.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that such salts may exist as a hydrate.

Examples of salts of the compounds of the present invention include (3S,4aR,6R,8aR)-6-[2-(1H-Tetrazol-5-yl)-ethyl]-1,2,3,4,4a,5,6,7,8,8a-decahydro-isoquinoline-3-carboxylic acid 2-ethyl-butyl ester trifluoroacetate salt; (3S, 4aR,6R,8aR)-6-[2-(1H-Tetrazol-5-yl)-ethyl]-1,2,3,4,4a,5,6, 7,8,8a-decahydro-isoquinoline-3-carboxylic acid isobutyl ester trifluoroacetate salt; (3S,4aR,6R,8aR)-6-[2-(1H-Tetrazol-5-yl)-ethyl]-1,2,3,4,4a,5,6,7,8,8a-decahydro-isoquinoline-3-carboxylic acid 3-methyl butyl ester trifluoroacetate salt; (3S,4aR,6R,8aR)-6-[2-(1H-Tetrazol-5-yl)-ethyl]-1,2,3,4,4a,5,6,7,8,8a-decahydro-isoquinoline-3-carboxylic acid decyl ester trifluoroacetate salt; and (3S,4aR,6R,8aR)-6-[2-(1H-Tetrazol-5-yl)-ethyl]-1,2,3,4,4a,5,6,7,8,8a-decahydro-isoquinoline-3-carboxylic acid ethyl ester hydrochloride salt.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formula I can be resolved by one of ordinary skill in the art using standard techniques well known in the art, such as those described by J. Jacques, et al., "Enantiomers, Racemates, and Resolutions", John Wiley and Sons, Inc., 1981.

The compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The specific stereoisomers and enantiomers of compounds of formula (I) can be prepared by one of ordinary skill in the art utilizing well known techniques and processes, such as those disclosed by Eliel and Wilen, "Stereochemistry of Organic Compounds", John Wiley & Sons, Inc., 1994, Chapter 7, Separation of Stereoisomers. Resolution. Racemization, and by Collet and Wilen, "Enantiomers, Racemates, and Resolutions", John Wiley & Sons, Inc., 1981. For example, the specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

The compounds of formula I can be prepared by techniques and procedures readily available to one of ordinary skill in the art. More specifically, compounds of Formula I can be chemically prepared, for example, by following the synthetic routes set forth in the Scheme below. However, the following discussion is not intended to be limiting to the scope of the present invention in any way. For example, the specific synthetic steps for the route described herein may be combined in different ways to prepare the compounds of Formula I. All substituents, unless otherwise indicated, are as previously defined. The reagents and starting materials are readily available to one of ordinary skill in the art. For example, certain starting materials can be prepared by one of ordinary skill in the art following procedures disclosed in U.S. Pat. No. 5,356,902 (issued Oct. 18, 1994) and U.S. Pat. No. 5,446,051 (issued Aug. 29, 1995) and U.S. Pat. No. 5,670,516 (issued Sep. 23, 1997) the entire contents, all of which, are herein incorporated by reference. Other necessary reagents and starting materials for the below procedures may be made by procedures which are selected from standard techniques of organic and heterocyclic chemistry, techniques which are analogous to the syntheses of known structurally similar compounds, and the procedures described in the Examples, including any novel procedures.

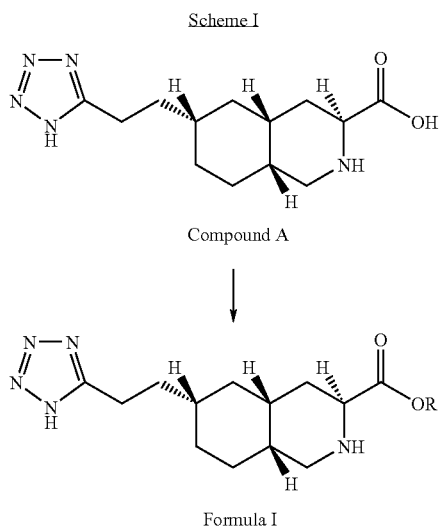

Scheme I

Compound A

Formula I

In Scheme I, compound A is esterified to provide the monoester of formula I under standard conditions well known in the art. For example, compound A is dissolved in a suitable organic solvent and treated with a suitable acid, such as hydrochloric acid.

Examples of suitable organic solvents include, methyl alcohol, ethyl alcohol, propyl alcohol, isopropyl alcohol, n-butyl alcohol, isobutyl alcohol, t-butyl alcohol, pentyl alcohol, isopentyl alcohol; hexyl alcohol, 3-methylpentyl alcohol, 2-ethylbutyl alcohol, n-heptyl alcohol, n-octyl alcohol, decyl alcohol and the like. The reaction is heated at about 40° C. to about 60° C. for about 4 hours to about 16 hours. The product is then isolated and purified using techniques well known to one of ordinary skill in the art, such as extraction techniques and chromatography.

For example, the above reaction is cooled, diluted with a suitable organic solvent, such as ethyl acetate, washed with saturated sodium bicarbonate, brine, dried over anhydrous magnesium sulfate, filtered and concentrated under vacuum to provide the compound of formula I. This material may be further purified by flash chromatography on silica gel with a suitable eluent such as ethyl acetate/hexane.

Alternatively, compound A is dissolved in a suitable organic solvent and treated with an excess of thionyl chloride. Examples of suitable organic solvents are anhydrous methyl alcohol, ethyl alcohol, propyl alcohol, isopropyl alcohol, butyl alcohol, isobutyl alcohol, t-butyl alcohol, pentyl alcohol, isopentyl alcohol, hexyl alcohol, 3-methylpentyl alcohol, 2-ethylbutyl alcohol, n-heptyl alcohol, n-octyl alcohol, decyl alcohol and the like.

The solution is stirred at reflux for about 1 to 3 hours, and at room temperature for about 8 to 16 hr. The mixture is then concentrated under vacuum, and the residue is purified in a manner analogous to the procedures described above to provide the prodrug monoester of formula I.

The pharmaceutically acceptable salts of formula I are readily prepared by one of ordinary skill in the art using standard techniques and procedures. For example, the above product is suspended in diethyl ether, which has been saturated with HCl gas. The mixture is stirred for about 1 to 3 hours. The precipitate is then filtered and washed with diethyl ether under vacuum to provide the pharmaceutically acceptable salt of the prodrug monoester of formula I.

The following examples represent typical syntheses of the compounds of formula I as described generally above. These examples are illustrative only and are not intended to limit the invention in any way. The reagents and starting materials are readily available to one of ordinary skill in the art. As used herein, the following terms have the meanings indicated: "eq" or "equiv." refers to equivalents; "g" refers to grams; "mg" refers to milligrams; "L" refers to liters; "mL" refers to milliliters; "μL" refers to microliters; "mol" refers to moles; "mmol" refers to millimoles; "psi" refers to pounds per square inch; "min" refers to minutes; "h" refers to hours; "° C." refers to degrees Celsius; "TLC" refers to thin layer chromatography; "HPLC" refers to high performance liquid chromatography; "δ" refers to part per million down-field from tetramethylsilane; "THF" refers to tetrahydrofuran; "DMF" refers to N,N-dimethylformamide; "DMSO" refers to methyl sulfoxide; "aq" refers to aqueous; "EtOAc" refers to ethyl acetate; "iPrOAc" refers to isopropyl acetate; "MeOH" refers to methanol; "MTBE" refers to tert-butyl methyl ether, and "RT" refers to room temperature.

EXAMPLE 1

6-[2-(1H-Tetrazol-5-yl)-ethyl]-decahydro-isoquinoline-3-carboxylic acid 2-ethyl-butyl ester

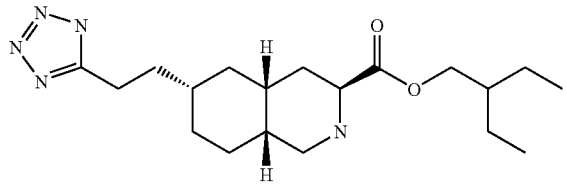

To a solution of 2.5 g (8.4 mmol) of 6-[2-(1H-Tetrazol-5-yl)-ethyl]-decahydro-isoquinoline-3-carboxylic acid monohydrate (prepared as described in J. Med. Chem., 39 (11), pp. 2232-2244, (1996) or U.S. Pat. No. 5,670,516 (issued Sep. 23, 1997)) in 20 ml of 2-ethyl-1-butanol, 6.8 ml (92.8 mmol) of thionyl chloride is added. The solution is stirred at 120° C. for 3 hr. The mixture is concentrated in vacuo and the residue washed with ethyl ether. The residue is purified by SPE (Oasis HLB) to afford the title compound.

Electrospray Mass Spectrum: M+1=364.

EXAMPLE 2

6-[2-(1H-Tetrazol-5-yl)-ethyl]-decahydro-isoquinoline-3-carboxylic acid isobutyl ester

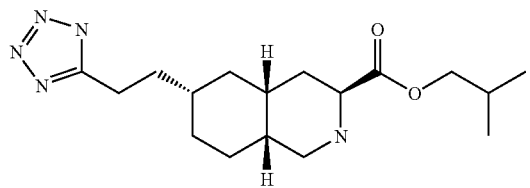

Prepared according to the procedures essentially as described in Example 1, above, using 20 mL of 2-methyl-1-propanol to afford of the title compound.
Electrospray Mass Spectrum: M+1=336.

EXAMPLE 3

6-[2-(2H-Tetrazol-5-yl)-ethyl]-decahydro-isoquinoline-3-carboxylic acid 3-methyl-butyl ester

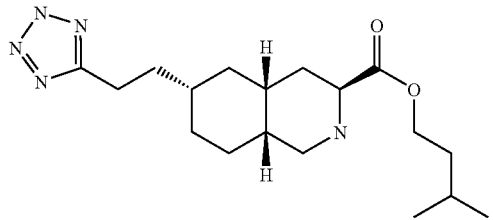

Prepared according to the procedures essentially as described in Example 1, above, using using 20 mL of 3-methyl-1-butanol to afford of the title compound.
Electrospray Mass Spectrum: M+1=350.

EXAMPLE 4

6-[2-(1H-Tetrazol-5-yl)-ethyl]-decahydro-isoquinoline-3-carboxylic acid decyl ester

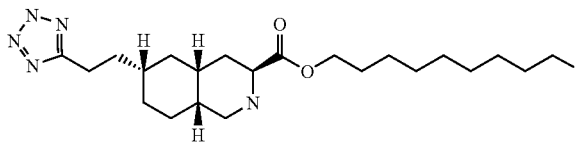

A solution of 2.5 g (8.4 mmol) of 6-[2-(1H-Tetrazol-5-yl)-ethyl]-decahydro-isoquinoline-3-carboxylic acid monohydrate in 50 ml decyl alcohol saturated with hydrogen chloride (g) is heated at 120° C. overnight. The mixture is concentrated in vacuo and the residue purified by SPE (Oasis HLB) to afford the title compound.
Electrospray Mass Spectrum: M+1=420.

EXAMPLE 5

6-[2-(2H-Tetrazol-5-yl)-ethyl]-decahydro-isoquinoline-3-carboxylic acid ethyl ester

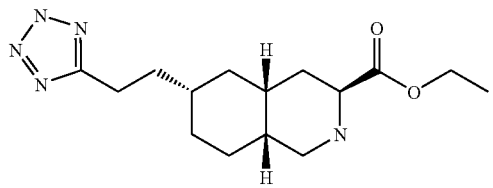

A solution of 6.0 g (21.5 mmol) of 6-[2-(1H-Tetrazol-5-yl)-ethyl]-decahydro-isoquinoline-3-carboxylic acid monohydrate in 70 mL of ethanol saturated with hydrogen chloride (g) is heated at reflux overnight. The mixture is concentrated in vacuo, suspended in diethyl ether, and again concentrated in vacuo. The residue is suspended in diethyl ether and heated at reflux for 3 hr. The solid is filtered and rinsed with diethyl ether to afford 7.4 g (100%) of the title compound.
Electrospray Mass Spectrum: M+1=308.

Particular Aspects of the Compounds of Formula I:

The following list sets out several groupings of particular substituents of the compounds of Formula I. It will be understood that the compounds of Formula I having such particular substituents represent particular aspects of the present invention. It will be further understood that each of these groupings may be combined with other provided groupings, to create still additional particular aspects of the present invention.

Thus, a particular aspect of the novel compounds of Formula I is one wherein:
(a) R represents $C_1$-$C_{10}$ alkyl, $C_2$-$C_6$ alkenyl, $C_1$-$C_6$ alkyl-aryl, $C_1$-$C_6$ alkyl-($C_3$-$C_{10}$)cycloalkyl, $C_1$-$C_6$ alkyl-N,N—$C_1$-$C_6$ dialkylamine, $C_1$-$C_6$ alkyl-pyrrolidine, $C_1$-$C_6$ alkyl-piperidine, $C_1$-$C_6$ alkyl-morpholine;
(b) R represents $C_1$-$C_{10}$ alkyl or $C_2$-$C_6$ alkenyl;
(c) R represents $C_1$-$C_{10}$ alkyl or $C_1$-$C_6$ alkyl-aryl;
(d) R represents $C_1$-$C_{10}$ alkyl or $C_1$-$C_6$ alkyl-($C_3$-$C_{10}$)cycloalkyl;
(e) R represents $C_1$-$C_{10}$ alkyl or $C_1$-$C_6$ alkyl-N,N—$C_1$-$C_6$ dialkylamine;
(f) R represents $C_1$-$C_{10}$ alkyl or $C_1$-$C_6$ alkyl-pyrrolidine;
(g) R represents $C_1$-$C_{10}$ alkyl or $C_1$-$C_6$ alkyl-piperidine;
(h) R represents $C_1$-$C_{10}$ alkyl or $C_1$-$C_6$ alkyl-morpholine;
(i) R represents $C_1$-$C_{10}$ alkyl;
(j) R represents 2-ethyl butyl, isobutyl, 3-methyl butyl, decyl, or ethyl; or
(k) R represents ethyl Pharmacological Results The following in vivo data, in rats, dogs and monkeys, exemplify the improvement in bioavailability of the monoester prodrugs of the present invention over the monoacid of (3S,4aR,6R,8aR)-6-[2-(1(2)H-tetrazole-5-yl)ethyl-1,2,3,4,4a,5,6,7,8,8a-decahydroisoquinoline-3-carboxylic acid.

Percent bioavailability is determined using the following equation:

$$\frac{\text{AUC p.o.}}{\text{AUC i.v.}} \times \frac{\text{dose i.v.}}{\text{dose p.o.}} \times 100 = \% \text{ Bioavailability}$$

wherein AUC represents the area under the curve, p.o. represents oral dose, and i.v. represents intravenous dose.

Bioavailability in Dogs:

Beagle dogs (2 male and 1 female) are administered an oral dose, and later an iv dose of (3S,4aR,6R,8aR)-6-[2-(1(2)H-tetrazole-5-yl)ethyl-1,2,3,4,4a,5,6,7,8,8a-decahydroisoquinoline-3-carboxylic acid (10 mg/Kg p.o; 1 mg/Kg i.v.) to determine oral bioavailability. Subsequently, the same three dogs are administered an oral 10 mg/kg dose of an ester prodrug (for example (3S,4aR,6R,8aR)-6-[2-(1(2)H-tetrazole-5-yl)ethyl-1,2,3,4,4a,5,6,7,8,8a-decahydroisoquinoline-3-carboxylic acid ethyl ester, HCL salt) to determine whether the prodrug would increase bioavailability of the parent acid. The plasma concentrations of (3S,4aR,6R, 8aR)-6-[2-(1(2)H-tetrazole-5-yl)ethyl-1,2,3,4,4a,5,6,7,8,8a-decahydroisoquinoline-3-carboxylic acid are determined by LC/MS/MS.

Study Methods:

Live Phase: (3S,4aR,6R,8aR)-6-[2-(1(2)H-tetrazole-5-yl)ethyl-1,2,3,4,4a,5,6,7,8,8a-decahydroisoquinoline-3-carboxylic acid (HCl salt) is dissolved in dilute sodium hydroxide for oral administration (30 mg/ml) and in 10% ethanol/water for iv administration (10 mg/ml). (3S,4aR,6R,8aR)-6-[2-(1(2)H-tetrazole-5-yl)ethyl-1,2,3,4,4a,5,6,7,8,8a-decahydroisoquinoline-3-carboxylic acid ethyl ester, HCL salt is dissolved in water for oral administration (30 mg/ml). Dogs weighed between 12 to 15 kg.

Results:

The oral bioavailability for 3S,4aR,6R,8aR)-6-[2-(1(2)H-tetrazole-5-yl)ethyl-1,2,3,4,4a,5,6,7,8,8a-decahydroisoquinoline-3-carboxylic acid was determined to be 18% in dogs. When 3S,4aR,6R,8aR)-6-[2-(1(2)H-tetrazole-5-yl)ethyl-1,2,3,4,4a,5,6,7,8,8a-decahydroisoquinoline-3-carboxylic acid ethyl ester (HCL salt) was administered, bioavailability increased to 33.1%. The use of the prodrug form 3S,4aR,6R,8aR)-6-[2-(1(2)H-tetrazole-5-yl)ethyl-1,2,3,4,4a,5,6,7,8,8a-decahydroisoquinoline-3-carboxylic acid ethyl ester (HCL salt), provided approximately a 2 fold increase in bioavailability over the parent acid.

Tables 1 below summarizes the pharmacokinetic parameters found for Compounds A and B following 1 mg/kg administration (i.v.) or 10 mg/kg administration (p.o.) to Beagle Dogs.

TABLE 1

Pharmacokinetic Parameters of Compound A in Beagle Dogs after a 1 mg/kg dose of Compound A (i.v.) and a 10 mg/kg dose of Compound A or the ethyl ester Prodrug, Compound B (p.o.).

| Compound | $T_{max}$ (hr) | $C_{max}$ (ng/mL) | AUC (ng hr/mL) | % Bioavail | Improvement |
|---|---|---|---|---|---|
| A (acid), i.v. (1 mg/kg) | — | 2,820 | 4,220 | — | — |
| A (acid), p.o. (10 mg/kg) | 4 | 1,227 | 7,577 | 18.0 | 1 |
| B (ester), p.o. (10 mg/kg) | 4 | 1,662 | 13,953 | 33.1 | ~2X |

Bioavailability in Rats

Male Fischer Rats are administered either an oral or iv dose of (3S,4R,6R,8aR)-6-[2-(1(2)H-tetrazole-5-yl)ethyl-1,2,3,4,4a,5,6,7,8,8a-decahydroisoquinoline-3-carboxylic acid (10 mg/Kg) to determine oral bioavailability. A separate group of rats are administered an oral 10 mg/kg dose of an ester prodrug (for example (3S,4aR,6R,8aR)-6-[2-(1(2)H-tetrazole-5-yl)ethyl-1,2,3,4,4a,5,6,7,8,8a-decahydroisoquinoline-3-carboxylic acid ethyl ester, HCL salt) to determine whether the prodrug would increase bioavailability of the parent acid. The plasma concentrations of (3S,4aR,6R,8aR)-6-[2-(1(2)H-tetrazole-5-yl)ethyl-1,2,3,4,4a,5,6,7,8,8a-decahydroisoquinoline-3-carboxylic acid are determined by LC/MS/MS.

Results:

The oral bioavailability for 3S,4aR,6R,8aR)-6-[2-(1(2)H-tetrazole-5-yl)ethyl-1,2,3,4,4a,5,6,7,8,8a-decahydroisoquinoline-3-carboxylic acid was determined to be 3.6% in rats. When 3S,4aR,6R,8aR)-6-[2-(1(2)H-tetrazole-5-yl)ethyl-1,2,3,4,4a,5,6,7,8,8a-decahydroisoquinoline-3-carboxylic acid ethyl ester (HCL salt) was administered, bioavailability increased to 17.7%. The use of the prodrug form 3S,4aR,6R,8aR)-6-[2-(1(2)H-tetrazole-5-yl)ethyl-1,2,3,4,4a,5,6,7,8,8a-decahydroisoquinoline-3-carboxylic acid ethyl ester (HCL salt), provided approximately a 5 fold increase in bioavailability over the parent acid.

Tables 2 below summarizes the pharmacokinetic parameters found for Compounds A and B.

TABLE 2

Pharmacokinetic Parameters of Compound A in Fischer Rats after a 10 mg/kg Dose of Compound A or the ester Prodrug, Compound B.*

| Compound | $T_{max}$ (hr) | $C_{max}$ (ng/mL) | AUC (ng hr/mL) | % Bioavail | Improvement |
|---|---|---|---|---|---|
| A (acid), i.v. | — | 11,022 | 6,727 | — | — |
| A (acid), p.o. | | 93 | 241 | 3.6 | 1 |
| B (ester), p.o. | | 265 | 1,192 | 17.7 | ~5X |

Bioavailability in Cynomolgus Monkeys

Two male and two female monkeys are administered an oral, and later, an iv dose of (3S,4aR,6R,8aR)-6-[2-(1(2)H-tetrazole-5-yl)ethyl-1,2,3,4,4a,5,6,7,8,8a-decahydroisoquinoline-3-carboxylic acid (oral: 3 mg/kg; iv: 0.3 mg/kg) to determine oral bioavailability. The same animals are also subsequently administered an oral 3 mg/kg dose of (3S,4aR,6R,8aR)-6-[2-(1(2)H-tetrazole-5-yl)ethyl-1,2,3,4,4a,5,6,7,8,8a-decahydroisoquinoline-3-carboxylic acid ethyl ester to determine if the ester prodrug form increases bioavailability of the parent acid. The plasma concentrations of the parent acid are determined by LC/MS/MS.

Study Design

Four cynomolgus monkeys (2/sex) are given a single oral dose of (3S,4aR,6R,8aR)-6-[2-(1(2)H-tetrazole-5-yl)ethyl-1,2,3,4,4a,5,6,7,8,8a-decahydroisoquinoline-3-carboxylic acid (3 mg/kg) on day 0, a single iv dose of (3S,4aR,6R,8aR)-6-[2-(1(2)H-tetrazole-5-yl)ethyl-1,2,3,4,4a,5,6,7,8,8a-decahydroisoquinoline-3-carboxylic acid (0.3 mg/kg) on day 4 and a single oral dose of (3S,4aR,6R,8aR)-6-[2-(1(2)H-tetrazole-5-yl)ethyl-1,2,3,4,4a,5,6,7,8,8a-decahydroisoquinoline-3-carboxylic acid ethyl ester (3 mg/kg) on day 8. Blood samples are collected at 0.5, 1, 2, 3, 4, 5, 6 and 8 hours post dose for oral dosing and 0.167, 0.33, 0.67, 1, 1.5, 2, 3 and 4 hours post dose for iv dosing. Dosing solutions for both the acid and ester are prepared in 0.9% sodium chloride.

Results:

The oral bioavailability for (3S,4aR,6R,8aR)-6-[2-(1(2)H-tetrazole-5-yl)ethyl-1,2,3,4,4a,5,6,7,8,8a-decahydroisoquinoline-3-carboxylic acid was determined to be 4.5% in monkeys. When (3S,4aR,6R,8aR)-6-[2-(1(2)H-tetrazole-5-yl)ethyl-1,2,3,4,4a,5,6,7,8,8a-decahydroisoquinoline-3-carboxylic acid ethyl ester (HCL salt) was administered, bioavailability increased to 11.4%. The use of the prodrug form (3S,4aR,6R,8aR)-6-[2-(1(2)H-tetrazole-5-yl)ethyl-1,2,3,4,4a,5,6,7,8,8a-decahydroisoquinoline-3-carboxylic acid ethyl ester (HCL salt), provided approximately a 2.5 fold increase in bioavailability over the parent acid.

Table 3 below summarizes the pharmacokinetic parameters found for Compounds A and B following i.v. or oral administration to Cynomolgus Monkeys.

TABLE 3

Pharmacokinetic Parameters of Compound A in Cynomolgus Monkeys after an i.v. and p.o. Dose of Compound A or the ester Prodrug, Compound B.

| Compound | $T_{max}$ (hr) | $C_{max}$ (ng/mL) | AUC (ng hr/mL) | % Bioavail | Improvement |
|---|---|---|---|---|---|
| A (acid), i.v. (.3 mg/kg) | — | 1,622 | 1,076 | — | |
| A (acid), p.o. (3 mg/kg) | 6 | 77 | 479 | 4.5 | 1 |
| B (ester), p.o. (3 mg/kg) | 2 | 301 | 1225 | 11.4 | ~2.5X |

The present invention further provides a method of antagonizing the AMPA or GluR$_5$ receptors, of the larger class of excitatory amino acid receptors, which comprises administering to a patient an effective amount of a compound of formula I. The excessive or inappropriate stimulation of excitatory amino acid receptors leads to neuronal cell damage or loss by way of a mechanism known as excitotoxicity. This process has been suggested to mediate neuronal degeneration in a variety of neurological disorders and conditions. The medical consequences of such neuronal degeneration makes the abatement of these degenerative neurological processes an important therapeutic goal. For instance, excitatory amino acid receptor excitotoxicity has been implicated in the pathophysiology of numerous neurological disorders, including the etiology of cerebral deficits subsequent to cardiac bypass surgery and grafting, stroke, cerebral ischemia, spinal cord lesions resulting from trauma or inflammation, perinatal hypoxia, cardiac arrest, and hypoglycemic neuronal damage. In addition, excitotoxicity has been implicated in chronic neurodegenerative conditions including Alzheimer's Disease, Huntington's Chorea, inherited ataxias, AIDS-induced dementia, amyotrophic lateral sclerosis, idiopathic and drug-induced Parkinson's Disease, as well as ocular damage and retinopathy. Other neurological disorders implicated with excitotoxicity and/or glutamate dysfunction include muscular spasticity including tremors, drug tolerance and withdrawal, brain edema, convulsive disorders including epilepsy, depression, anxiety and anxiety related disorders such as post-traumatic stress syndrome, tardive dyslinesia, and psychosis related to depression, schizophrenia, bipolar disorder, mania, and drug intoxication or addiction (see generally U.S. Pat. Nos. 5,446,051 and 5,670,516). Excitatory amino acid receptor antagonists may also be useful as analgesic agents and for treating or preventing various forms of headache, including cluster headache, tension-type headache, and chronic daily headache. In addition, published International Patent application WO 98/45720 reports that excitatory amino acid receptor excitotoxicity participates in the etiology of acute and chronic pain states including severe pain, intractable pain, neuropathic pain, post-traumatic pain.

It is also known that trigeminal ganglia, and their associated nerve pathways, are associated with painful sensations of the head and face such as headache and, in particular, migraine. Moskowitz (*Cephalalgia*, 12, 5-7, (1992) proposed that unknown triggers stimulate the trigeminal ganglia which in turn innervate vasculature within cephalic tissue, giving rise to the release of vasoactive neuropeptides from axons innervating the vasculature. These neuropeptides initiate a series of events leading to neurogenic inflammation of the meninges, a consequence of which is pain. This neurogenic inflammation is blocked by sumatriptan at doses similar to those required to treat acute migraine in humans. However, such doses of sumatriptan are associated with contraindications as a result of sumatriptan's attendant vasoconstrictive properties. (see MacIntyre, P. D., et al., *British Journal of Clinical Pharmacology*, 34, 541-546 (1992); Chester, A. H., et al., *Cardiovascular Research*, 24, 932-937 (1990); Conner, H. E., et al., *European Journal of Pharmacology*, 161, 91-94 (1990)). Recently, it has been reported that all five members of the kainate subtype of ionotropic glutamate receptors are expressed on rat trigeminal ganglion neurons, and in particular, high levels of GluR$_5$ and KA2 have been observed. (Sahara et al., *The Journal of Neuroscience*, 17(17), 6611 (1997)). As such, migraine presents yet another neurological disorder which may be implicated with glutamate receptor excitotoxicity.

The use of a neuroprotective agent, such as an excitatory amino acid receptor antagonist, is believed to be useful in treating or preventing all of the aforementioned disorders and/or reducing the amount of neurological damage associated with these disorders. For example, studies have shown that AMPA receptor antagonists are neuroprotective in focal and global ischemia models. The competitive AMPA receptor antagonist NBQX (2,3-dihydroxy-6-nitro-7-sulfamoyl-benzo[f]quinoxaline) has been reported effective in preventing global and focal ischemic damage. Sheardown et al., *Science*, 247, 571 (1900); Buchan et al., *Neuroreport*, 2, 473 (1991); LePeillet et al., *Brain Research*, 571, 115 (1992). The noncompetitive AMPA receptor antagonists GKYI 52466 has been shown to be an effective neuroprotective agent in rat global ischemia models. LaPeillet et al., *Brain Research*, 571, 115 (1992). European Patent Application Publication No. 590789A1 and U.S. Pat. Nos. 5,446,051 and 5,670,516 disclose that certain decahydroisoquinoline derivative compounds are AMPA receptor antagonists and, as such, are useful in the treatment of a multitude of disorders conditions, including pain and migraine headache. WO 98/45270 discloses that certain decahydroisoquinoline derivative compounds are selective antagonists of the iGluR$_5$ receptor and are useful for the treatment of various types of pain, including; severe, chronic, intractable, and neuropathic pain.

As such, the compounds of the present invention are believed to be useful for treating neurological disorders, as discussed above. Such compounds could address a long felt need for safe and effective treatments for nerulogical disorders, without attending side effects. Thus, the present invention further provides a method for the treatment of a neurological disorder, which comprises administering to a patient in need thereof, an effective amount of a compound of formula I. More particularly, the present invention further provides a method for the treatment of pain or migraine, which comprises administering to a patient in need thereof, an effective amount of a compound of formula I. The treatment of neurological disorders and neurodegenerative diseases is hereby furthered.

As used herein the term "patient" refers to a mammal, such a mouse, guinea pig, rat, dog, monkey, or human. It is understood that the preferred patient is a human.

The term "treating" (or "treat") as used herein includes its generally accepted meaning which encompasses prohibiting, preventing, restraining, and slowing, stopping, or reversing progression, severity, of a resultant symptom. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment.

An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

In effecting treatment of a patient afflicted with a condition, disease or disorder described above, a compound of formula (I) can be administered in any form or mode which makes the parent monoacid compound bioavailable in effective amounts, including oral and parenteral routes. For example, compounds of formula (I) can be administered orally, subcutaneously, intramuscularly, intravenously, transdermally, intranasally, rectally, buccally, and the like. Alternatively, the compound may be administered by continuous infusion. Oral administration is generally preferred. One skilled in the art of preparing formulations can readily select the proper form and mode of administration depending upon the particular characteristics of the compound selected, the disease state to be treated, the stage of the disease, and other relevant circumstances.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

According to another aspect, the present invention provides a pharmaceutical composition, which comprises a compound of formula I or a pharmaceutically acceptable salt thereof as defined hereinabove and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1

Hard gelatin capsules are prepared using the following ingredients:

|  | Quantify (mg/capsule) |
| --- | --- |
| Prodrug | 250 |
| Starch, dried | 200 |
| Magnesium Stearate | 10 |
| Total | 460 |

The above ingredients are mixed and filled into hard gelatin capsules in 460 mg quantities.

Formulation 2

Tablets each containing 60 mg of active ingredient are made as follows:

|  | Quantity (mg/tablet) |
| --- | --- |
| Prodrug | 60 |
| Starch | 45 |
| Microcrystalline Cellulose | 35 |
| Polyvinylpyrrolidone | 4 |
| Sodium Carboxymethyl Starch | 4.5 |
| Magnesium Stearate | 0.5 |
| Talc | 1 |
| Total | 150 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

What is claimed is:

1. A compound of the formula:

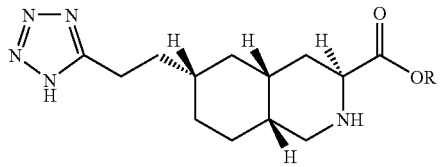

wherein R represents $C_2$-$C_{10}$ alkyl, or a pharmaceutically acceptable salt thereof.

2. The compound or salt according to claim 1 wherein R represents 2-ethyl-butyl, isobutyl, 3-methyl-butyl, decyl, or ethyl.

3. The compound or salt according to claim 2 wherein R represents 2-ethyl-butyl.

4. The compound or salt according to claim 2 wherein R represents isobutyl.

5. The compound or salt according to claim 2 wherein R represents 3-methyl-butyl.

6. The compound or salt according to claim 2 wherein R represents decyl.

7. The compound or salt according to claim 2 wherein R represents ethyl.

8. A salt selected from the group consisting of (3S,4aR,6R,8aR)-6-[2-(1H-Tetrazol-5-yl)-ethyl]-1,2,3,4,4a,5,6,7,8,8a-decahydro-isoquinoline-3-carboxylic acid 2-ethyl-butyl ester trifluoroacetate salt; (3S,4aR,6R,8aR)-6-[2-(1H-Tetrazol-5-yl)-ethyl]-1,2,3,4,4a,5,6,7,8,8a-decahydro-isoquinoline-3-carboxylic acid isobutyl ester trifluoroacetate salt; (3S,4aR,6R,8aR)-6-[2-(1H-Tetrazol-5-yl)-ethyl]-1,2,3,4,4a,5,6,7,8,8a-decahydro-isoquinoline-3-carboxylic acid 3-methyl butyl ester trifluoroacetate salt; (3S,4aR,6R,8aR)-6-[2-(1H-Tetrazol-5-yl)-ethyl]-1,2,3,4,4a,5,6,7,8,8a-decahydro-isoquinoline-3-carboxylic acid decyl ester trifluoroacetate salt; and (3S,4aR,6R,8aR)-6-[2-(1H-Tetrazol-5-yl)-ethyl]-1,2,3,4,4a,5,6,7,8,8a-decahydro-isoquinoline-3-carboxylic acid ethyl ester hydrochloride salt.

9. A compound which is (3S,4aR,6R,8aR)-6-[2-(1H-Tetrazol-5-yl)-ethyl]-1,2,3,4,4a,5,6,7,8,8a-decahydro-isoquinoline-3-carboxylic acid 2-ethyl-butyl ester.

10. A compound which is (3S,4aR,6R,8aR)-6-[2-(1H-Tetrazol-5-yl)-ethyl]-1,2,3,4,4a,5,6,7,8,8a-decahydro-isoquinoline-3-carboxylic acid isobutyl ester.

11. A compound which is (3S,4aR,6R,8aR)-6-[2-(1H-Tetrazol-5-yl)-ethyl]-1,2,3,4,4a,5,6,7,8,8a-decahydro-isoquinoline-3-carboxylic acid 3-methyl butyl ester.

12. A compound which is (3S,4aR,6R,8aR)-6-[2-(1H-Tetrazol-5-yl)-ethyl]-1,2,3,4,4a,5,6,7,8,8a-decahydro-isoquinoline-3-carboxylic acid decyl ester.

13. A compound which is (3S,4aR,6R,8aR)-6-[2-(1H-Tetrazol-5-yl)-ethyl]-1,2,3,4,4a,5,6,7,8,8a-decahydro-isoquinoline-3-carboxylic acid ethyl ester.

14. (3S,4aR,6R,8aR)-6-[2-(1H-Tetrazol-5-yl)-ethyl]-1,2,3,4,4a,5,6,7,8,8a-decahydro-isoquinoline-3-carboxylic acid methyl ester, or a pharmaceutically acceptable salt thereof, in isolated form.

15. A pharmaceutical composition which comprises a compound of the formula:

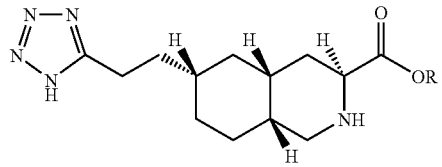

wherein R represents $C_1$-$C_{10}$ alkyl, or a pharmaceutically acceptable salt thereof, and a pharmaceutically acceptable diluent or carrier.

16. The pharmaceutical composition according to claim 15 which comprises (3S,4aR,6R,8aR)-6-[2-(1H-Tetrazol-5-yl)-ethyl]-1,2,3,4,4a,5,6,7,8,8a-isoquinoline-3-carboxylic acid 2-ethyl-butyl ester, or pharmaceutically acceptable salt thereof; (3S,4aR,6R,8aR)-6-[2-(1H-Tetrazol-5-yl)-ethyl]-1,2,3,4,4a,5,6,7,8,8a-decahydro-isoquinoline-3-carboxylic acid isobutyl ester, or pharmaceutically acceptable salt thereof; (3S,4aR,6R,8aR)-6-[2-(1H-Tetrazol-5-yl)-ethyl]-1,2,3,4,4a,5,6,7,8,8a-decahydro-isoquinoline-3-carboxylic acid 3-methyl-butyl ester, or a pharmaceutically acceptable salt thereof; (3S,4aR,6R,8aR)-6-[2-(1H-Tetrazol-5-yl)-ethyl]-1,2,3,4,4a,5,6,7,8,8a-decahydro-isoquinoline-3-carboxylic acid decyl ester, or a pharmaceutically acceptable salt thereof; or (3S,4aR,6R,8aR)-6-[2-(1H-Tetrazol-5-yl)-ethyl]-1,2,3,4,4a,5,6,7,8,8a-decahydro-isoquinoline-3-carboxylic acid ethyl ester, or a pharmaceutically acceptable salt thereof; and a pharmaceutically acceptable diluent or carrier.

17. A method of treating pain, which comprises administering to a patient an effective amount of a compound of the formula:

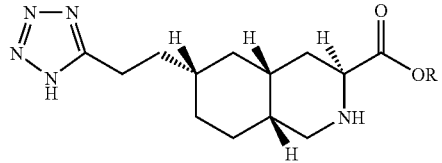

wherein R represents $C_1$-$C_{10}$ alkyl, or a pharmaceutically acceptable salt thereof.

18. The method according to claim 17, which comprises administering to a patient an effective amount of (3S,4aR,6R,8aR)-6-[2-(1H-Tetrazol-5-yl)-ethyl]-1,2,3,4,4a,5,6,7,8,8a-decahydro-isoquinoline-3-carboxylic acid 2-ethyl-butyl ester, or pharmaceutically acceptable salt thereof; (3S,4aR,6R,8aR)-6-[2-(1H-Tetrazol-5-yl)-ethyl]-1,2,3,4,4a,5,6,7,8,8a-decahydro-isoquinoline-3-carboxylic acid isobutyl ester, or pharmaceutically acceptable salt thereof; (3S,4aR,6R,8aR)-6-[2-(1H-Tetrazol-5-yl)-ethyl]-1,2,3,4,4a,5,6,7,8,8a-decahydro-isoquinoline-3-carboxylic acid 3-methyl-butyl ester, or a pharmaceutically acceptable salt thereof; (3S,4aR,6R, 8aR)-6-[2-(1H-Tetrazol-5-yl)-ethyl]-1,2,3,4,4a,5,6,7,8,8a-decahydro-isoquinoline-3-carboxylic acid decyl ester, or a pharmaceutically acceptable salt thereof; or (3S,4aR,6R,8aR)-6-[2-(1H-Tetrazol-5-yl)-ethyl]-1,2,3,4,4a,5,6,7,8,8a-decahydro-isoquinoline-3-carboxylic acid ethyl ester, or a pharmaceutically acceptable salt thereof.

19. A method of treating migraine, which comprises administering to a patient an effective amount of a compound of the formula:

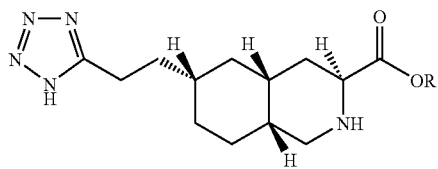

wherein R represents $C_1$-$C_{10}$ alkyl, or a pharmaceutically acceptable salt thereof.

20. The method according to claim 19, which comprises administering to a patient an effective amount of (3S,4aR,6R,8aR)-6-[2-(1H-Tetrazol-5-yl)-ethyl]-1,2,3,4,4a,5,6,7,8,8a-decahydro-isoquinoline-3-carboxylic acid 2-ethyl-butyl ester, or pharmaceutically acceptable salt thereof; (3S,4aR,6R,8aR)-6-[2-(1H-Tetrazol-5-yl)-ethyl]-1,2,3,4,4a,5,6,7,8,8a-decahydro-isoquinoline-3-carboxylic acid isobutyl ester, or pharmaceutically acceptable salt thereof; (3S,4aR,6R,8aR)-6-[2-(1H-Tetrazol-5-yl)-ethyl]-1,2,3,4,4a,5,6,7,8,8a-decahydro-isoquinoline-3-carboxylic acid 3-methyl-butyl ester, or a pharmaceutically acceptable salt thereof; (3S,4aR,6R,8aR)-6-[2-(1H-Tetrazol-5-yl)-ethyl]-1,2,3,4,4a,5,6,7,8,8a-decahydro-isoquinoline-3-carboxylic acid decyl ester, or a pharmaceutically acceptable salt thereof; or (3S,4aR,6R,8aR)-6-[2-(1H-Tetrazol-5-yl)-ethyl]-1,2,3,4,4a,5,6,7,8,8a-decahydro-isoquinoline-3-carboxylic acid ethyl ester, or a pharmaceutically acceptable salt thereof.

* * * * *